United States Patent [19]

Murljacic

[11] Patent Number: 5,766,006
[45] Date of Patent: Jun. 16, 1998

[54] TOOTH SHADE ANALYZER SYSTEM AND METHODS

[76] Inventor: Maryann Lehmann Murljacic, 21 Heather La., Darien, Conn. 06820

[21] Appl. No.: 494,979

[22] Filed: Jun. 26, 1995

[51] Int. Cl.$^6$ .................................................. A61C 19/10
[52] U.S. Cl. .............................................. 433/26; 356/408
[58] Field of Search .......................... 433/26, 29, 203.1, 433/215; 364/413.28; 356/402, 405, 406, 408

[56] References Cited

U.S. PATENT DOCUMENTS

| | | | |
|---|---|---|---|
| 3,986,777 | 10/1976 | Roll | 356/176 |
| 4,247,202 | 1/1981 | Failes | 356/310 |
| 4,414,635 | 11/1983 | Gast et al. | 364/526 |
| 4,518,258 | 5/1985 | Broersma | 356/405 |
| 4,547,074 | 10/1985 | Hinoda et al. | 356/405 |
| 4,623,973 | 11/1986 | Hoffrichter et al. | 364/526 |
| 4,654,794 | 3/1987 | O'Brien | 364/413 |
| 4,692,481 | 9/1987 | Kelly | 523/210 |
| 4,836,674 | 6/1989 | Lequime et al. | 356/319 |
| 4,881,811 | 11/1989 | O'Brien | 356/323 |
| 5,012,431 | 4/1991 | Stanziola | 364/526 |
| 5,124,797 | 6/1992 | Williams et al. | 433/29 |
| 5,231,472 | 7/1993 | Marcus et al. | 356/402 |
| 5,240,414 | 8/1993 | Thompson | 433/26 |
| 5,313,267 | 5/1994 | MacFarlene et al. | 356/405 |
| 5,373,364 | 12/1994 | Krzyminski | 356/405 |
| 5,383,020 | 1/1995 | Vieillefosse | 356/405 |

FOREIGN PATENT DOCUMENTS

| | | | |
|---|---|---|---|
| 0360657 | 3/1990 | European Pat. Off. . | |
| 4301530 | 10/1992 | Japan | 356/402 |
| 4338465 | 11/1992 | Japan | 433/203.1 |
| WO 86/03292 | 6/1986 | WIPO . | |
| 9102955 | 3/1991 | WIPO | 433/203.1 |

*Primary Examiner*—Cary E. O'Connor
*Attorney, Agent, or Firm*—Curtis A. Vock

[57] ABSTRACT

An intraoral camera connects to a shade analyzer subsystem, e.g., a digital video processor, and a color display monitor. The camera captures a digital color image of the patient's tooth and the subsystem compares that image to a stored plurality of tooth shades. Each tooth shade is represented in a block of data, including color image data, a tooth shade digital word, and a manufacturer type. The patient's tooth image includes an RGB chromaticity representation that is scanned and compared with the several tooth shades stored in memory, and a match is determined and communicated to a user of the system. The methodology includes the specification of fractional tooth shades, if needed, corresponding to a plurality of porcelain films for manufacturing a reconstructed tooth.

4 Claims, 8 Drawing Sheets

TOOTH SHADE ANALYZER SYSTEM AND METHODS

In dentistry, there has been a shift in recent years from a philosophy of drilling and filling to one of prevention and cosmetics. By way of example, many people today are choosing to have clinical procedures done to enhance their smile and appearance. Most of these procedures involve the modification of tooth shape, alignment, and/or color.

A necessary step in altering a patient's tooth color is to determine the "shade" of the existing tooth. For example, those persons seeking a whiter, brighter smile are still assessed to establish their existing tooth color so that an appropriate before and after comparison can be made. Shade determination is even more important for those persons seeking reconstructive work, since one goal of the reconstructive process is to achieve a natural appearance. Therefore, it is important to know the existing tooth shade so that it can be accurately matched with the new restoration.

The dental profession utilizes standardized shade guides created by those companies which manufacture the reconstructive materials. One well-known shade guide is the Vita™ shade guide, which includes sixteen different shades. Other, less popular shade guides include those guides provided by Bioform™ and SR-Vivaden™.

These shade guides are utilized in a rudimentary fashion. The guide itself is a plastic plate with a plurality of removable color tabs that are shaped like a tooth, e.g., the front tooth. Typically, to assess a patient's tooth shade, a dentist removes one of the colored tabs and holds it up to the patient's tooth so that she can "eyeball" the closest match possible. Understandably, there are many variables to this method, some of which stem from the subjectivity of the dentist making the eyeball assessment.

Once the tooth shade is determined, the information is used relative to the particular procedure needed. In bonding or filling a tooth, for example, the composite materials required for the restoration are specified within the range of the shade guide, e.g., one of sixteen shades for the Vita™ range. More particularly, if a crown, bridge or denture is needed, the patient's shade must be determined and communicated correctly to the lab that make the crown, bridge or denture.

The communication of shade information between the dentist and the lab is extremely important. Often, there is a break-down or failure in this communication, resulting in a poor shade match for the patient. In some cases, a particular dentist utilizes an uncommon shade guide, thereby leaving the lab technician to eyeball and convert the shade information to a Vita standard shade (since porcelain is often made from the Vita™ shade guide). This too can result in improper shade matching.

The process for selecting the porcelain for a particular tooth shade illustrates the difficulty in assessing and manufacturing the correct color match. If, for example, a crown of Vita™ shade A3 is desired, porcelain is built by hand with a paint brush onto a model of the tooth to be restored. The porcelain is built in layers on the model to achieve translucency and natural appearance. Each layer has a particular color and intensity associated with it. To generate shade A3, the technician follows a "recipe" that is given by the manufacturer Vident™, requiring a different shade for each layer of porcelain applied. If a doctor asks for a shade that is not a Vita™ standard shade, the technician typically seeks to achieve that shade by combining different porcelain shade combinations together, to increase or decrease the chroma, hue and value of the shade.

To further complicate the color-matching process, same dentists are simply not skilled in taking and determining shade information. Therefore, these dentists sometimes send their patients directly to the lab where the technician can determine the shade information. Alternatively, these dentists sometimes have a technician come to the office. In either event, there is, at times, one more level of subjective uncertainty injected into the correct match and determination of a patient's tooth shade.

It is, accordingly, an object of the invention to provide a shade analyzer system which reduces the afore-mentioned difficulties.

Still another object of the invention is to provide methodology for assessing and communicating a patient's tooth color in an objective manner.

These and other objects of the invention will become apparent in the description which follows.

SUMMARY OF THE INVENTION

In one aspect, the invention provides a system for determining the tooth shade of a patient's tooth. An intraoral camera captures the image of the patient's tooth, including color information representative of the tooth's color. A shade analyzer sub-system connects in electrical communication with the intraoral camera, and has (i) a color processing section for determining the color of the patient's tooth from the color information of the image; (ii) storage memory for storing shade information representative of a plurality of tooth shades (i.e., each of the tooth shades corresponds to a different tooth color), (iii) a color correlation section for comparing the color of the patient's tooth to the plurality of tooth shades and for identifying a tooth shade with a color corresponding to the color of the patient's tooth, and (iv) means such as a display terminal for communicating the identified tooth shade to a user of the system.

In another aspect, the system includes a monitor used to display the color image to a user of the system. The shade analyzer sub-system thus communicates a tooth color representative of the identified tooth shade to the monitor, thereby providing a user of the system with a visual comparison of the patient's tooth color with the color of the identified tooth shade.

In a further aspect, the color processing section determines RGB chromaticities of the color image, and each of the plurality of tooth shades has a corresponding RGB representation of the tooth color stored in memory. In such an aspect, the color correlation section quantitatively compares the RGB chromaticities with the RGB representation of each of the tooth shades, and compares and identifies a tooth shade based upon an comparison of the chromaticities and the RGB representations.

In still another aspect of the invention, the system associates one or more of the plurality of tooth shades with at least one standardized shade corresponding to a particular manufacturer's porcelain product. Accordingly, the system communicates the standardized shade to a user of the system so that the desired tooth may be constructed.

The color correlation section of the invention can also identify a combination of tooth shades having a combined color corresponding to the color of the patient's tooth. As such, the system can (i) associate each of the tooth shades in the combination with at least one standardized shade corresponding to an particular manufacturer's porcelain product, (ii) specify fractions of each of the standardized shades needed to form the combined color, and (iii) communicate information identifying the fractions of each of the tooth shades in the combination to a user of the system.

The invention also provides a tooth shade analyzer system for determining the tooth shade of a patient's tooth. One section of the analyzer communicates with an intraoral camera of the type which captures the image of the patient's tooth, including color information representative of a color of the tooth. Other sections of the analyzer (i) determines the color of the patient's tooth from the color information of the image, and (ii) stores shade information representative of a plurality of tooth shades. A color correlation section compares the color of the patient's tooth to the plurality of tooth shades and identifies one or more tooth shades with a combined color corresponding to the color of the patient's tooth. Finally, the system includes means for communicating with devices such as display monitors to communicate the one or more identified tooth shades to a user of the system. In this manner, the analyzer matches the patient's tooth with one or more corresponding tooth shades and assists in reconstructing the patient's tooth.

The invention also includes a method for determining the tooth shade of a patient's tooth, including the steps of: capturing the image of the patient's tooth with an intraoral camera, the image including color information representative of a color of the tooth; determining the color of the patient's tooth from the color information of the image; comparing the color of the patient's tooth to a plurality of tooth shades, the tooth shades being stored in an electronic medium; identifying one or more tooth shades with a combined color corresponding to the color of the patient's tooth; and communicating the one or more identified tooth shades to a user of the system.

A further method of the invention compares the tooth shade of a patient's tooth after the patient's teeth are cosmetically whitened, including the steps of: capturing a first image of the patient's tooth with an intraoral camera before the tooth is cosmetically whitened, the first image including first color information representative of a color of the tooth; processing the color information of the image to determine the color of the patient's tooth; comparing the color of the patient's tooth to a plurality of tooth shades, the tooth shades being stored in an electronic medium; identifying one or more tooth shades with a combined color corresponding to the color of the patient's tooth; whitening the teeth; communicating the one or more identified tooth shades to a user of the system; and viewing the patient's tooth on a monitor after the whitening step while simultaneously displaying an image of the patient's pre-whitened tooth, to provide before and after imagery.

In another aspect of the invention, a process is provided for manufacturing a reconstructive tooth for a patient, including the steps of: capturing the image of the patient's tooth with an intraoral camera, the image including color information representative of a color of the tooth; processing the color information of the image to determine the color of the patient's tooth; comparing the color of the patient's tooth to a plurality of tooth shades, the tooth shades being stored in an electronic medium; specifying one or more tooth shades, and any fractions thereof, having a combined color corresponding to the color of the patient's tooth; and painting one or more layers of porcelain onto a model of the patient's tooth, each of the layers of porcelain corresponding to the specified tooth shades and the fractions thereof.

The invention also includes a system for determining the tooth shade of a patient's tooth by utilzing color CCD cameras. In one aspect, a color CCD camera captures the image of the patient's tooth, including color information representative of a color of the tooth. A shade analyzer sub-system is connected for electrical communication with the CCD camera, and has (i) a color processing section for determining the color of the patient's tooth from the color information of the image, (ii) a storage section for storing shade information representative of a plurality of tooth shades, each of the tooth shades corresponding to a different tooth color, (iii) a color correlation section for comparing the color of the patient's tooth to the plurality of tooth shades and for identifying a tooth shade with a color corresponding to the color of the patient's tooth, and (iv) a section for communicating the identified tooth shade to a user of the system.

In accord with the invention, the CCD camera can include three CCD arrays, each of the arrays collecting image data corresponding to a color selected from the group of red, green and blue. Alternatively, the CCD camera can include a single CCD array, including a plurality of proximately located pixels corresponding to a color selected from the group of red, green and blue, each of any group of three pixels having a different color associated therewith.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF THE DRAWINGS

The use of intraoral video and/or imaging systems (hereinafter "intraoral camera system") has grown rapidly in dentistry over the past few years. Such systems are widely utilized in "show and tell" settings, i.e., where the dentist can show and illustrate particular features of a patient's mouth. However, these intraoral camera systems are rapidly becoming key to complex diagnostic and treatment planning. Presently, approximately 30% of the practicing dentists in the age group between about 35–54 own and utilize intraoral camera systems. It is expected that that percentage will only increase with increased familiarity. See *Dental Products Report* pgs. 22–24, February 1995.

Figure 1:
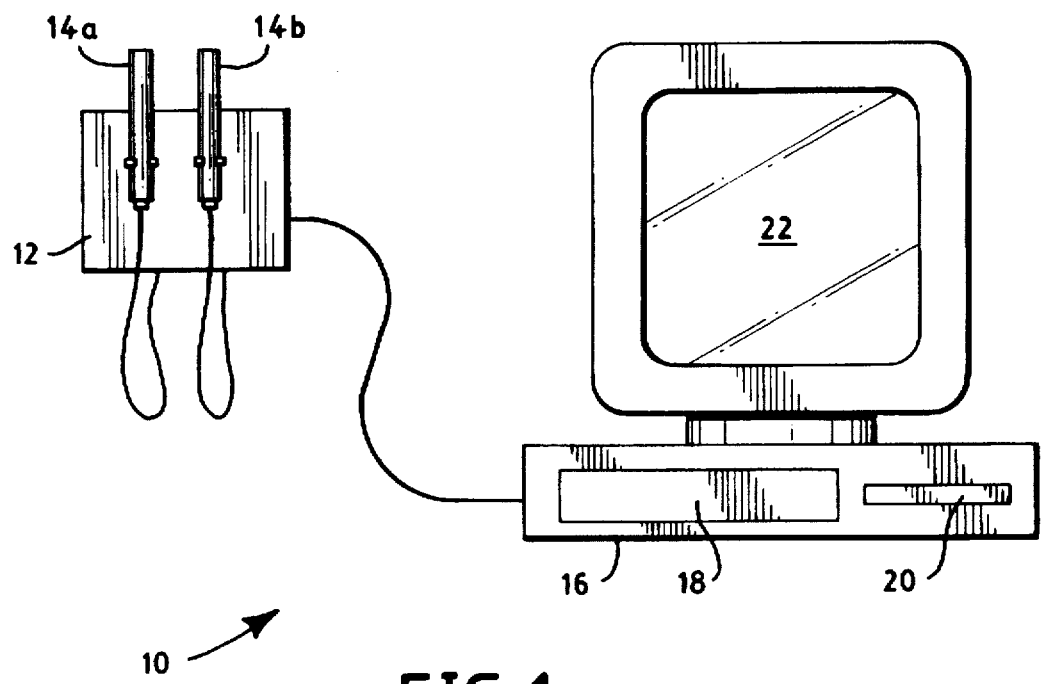
FIG. 1 shows a prior art intraoral camera system.

FIG. 1 illustrates a typical prior art intraoral camera system 10. The system 10 includes a wall-mounted intraoral camera 12, which includes twin halogen lamp light source (not shown) for uniform illuminance, one or more handpieces 14a, 14b, a digital video processor 16 (typically an IBM-compatible PC), which includes a hard drive 18 and floppy drive 20, and a color video monitor 22.

In operation, a dentist points a selected handpiece 14a, 14b at the target location within the patient's mouth to illuminate and view the resulting, full color image on the monitor 22. The endoscope handpieces 14a, 14b come in varying styles, including a wide angle configuration, e.g., a 100 degree field of view (FOV) for posterior and anterior views, and a near 0 degree FOV for full-arch and full-face images. The processor 16 provides storage for any selected image, and can further display selected close-ups on the monitor 22 through zoom capabilities.

There are several manufacturers of intraoral camera systems, offering an array of features. For example, Insight™, of San Carlos, Calif., offers a Power 0/100 similar to the one shown in FIG. 1. Other manufacturers include Cygnus Instruments, Inc. (CygnaScope™), of Goleta, Calif. VistaCam™ is yet another prior art intraoral camera system that incorporates a 90-degree FOV fiberoptic handpiece that delivers full color images from about 6 mm, i.e., the size of one typical tooth, to an image of the patient's whole smile.

Therefore, the prior art intraoral camera systems described above offer full color imagery of a patient's tooth. The image may be stored on disk 18, 20 and/or displayed on the screen 22.

Figure 2:
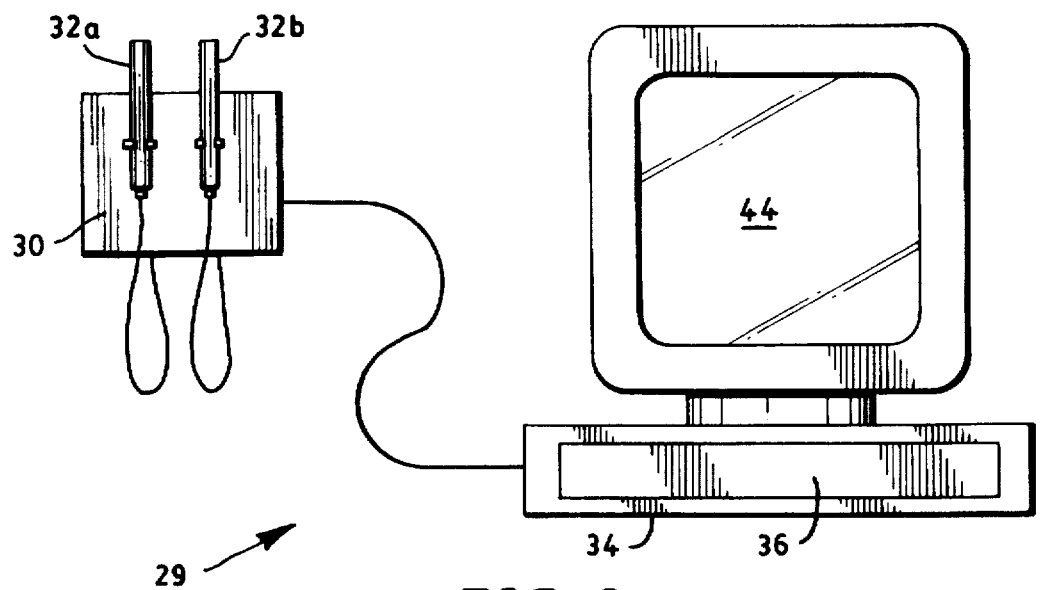
FIG. 2 illustrates a tooth shade analyzer system constructed according to the invention.

The invention makes use of an intraoral camera system of the type described above. Specifically, FIG. 2 illustrates one embodiment of the invention and which shows a tooth shade analyzer 29 including an intraoral camera 30, associated handpieces 32a, 32b, and a shade-analyzer subsystem 34. Preferably, the subsystem 34 is a digital video processor that is similar to the processor 16 of FIG. 1, and thus preferably includes the video processing capabilities of the processor 16, such as known to those skilled in the art. A storage medium 36, such as a hard disk 18 or floppy 20, stores digital color images of a plurality of tooth shades, such as each of the sixteen shades of the Vita™ shade guide. The storage medium 36 further stores any images collected by a user of the system 29.

Figure 3:
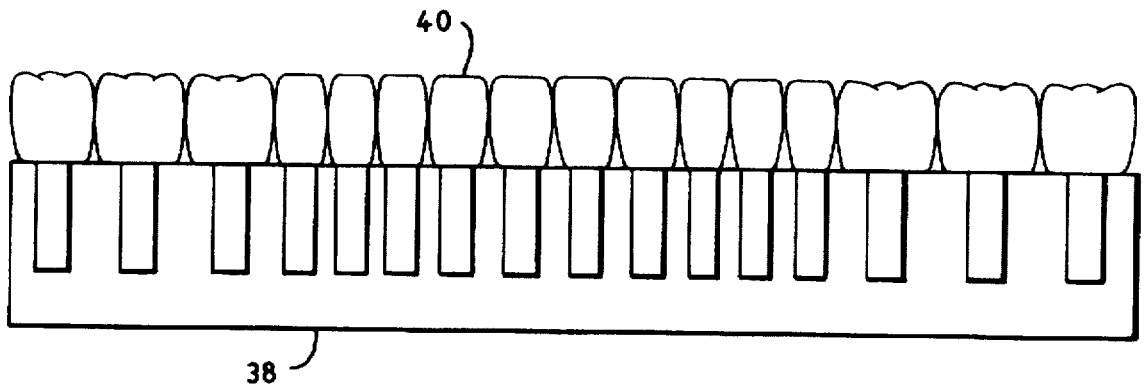
FIG. 3 illustrates a typical prior art tooth shade guide.
Figure 3A:
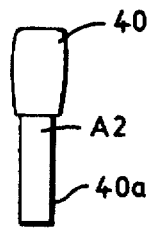
FIG. 3A illustrates one tooth shade tab of the shade guide of FIG. 3.

The storage of the digital color images of one or more shade guides is relatively straight-forward. In particular, FIG. 3 illustrates one shade guide 38 having sixteen separate tabs 40. Each of the tabs 40 is removable from the guide 38 so that it can be ported and viewed next to the patient's teeth. FIG. 3A illustrates one tab 40 that is removed from the guide 38. The tab holder 40a typically includes color information about the selected tab 40, here shown as shade "A2."

Figure 4:
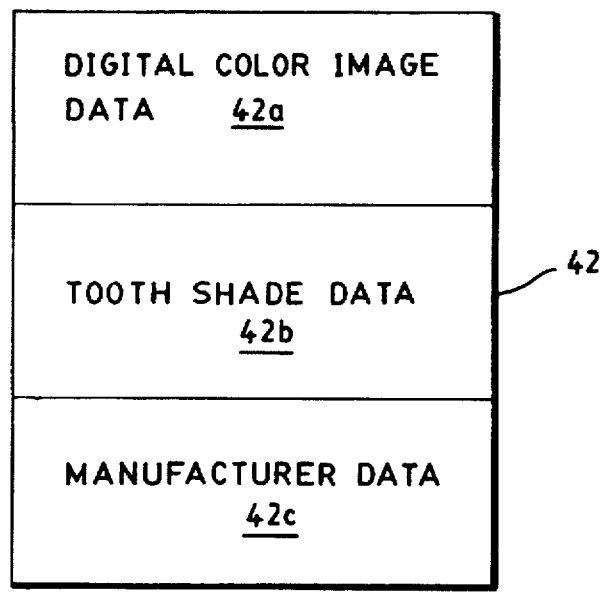
FIG. 4 illustrates a digital data block constructed according to the invention for specifying a tooth shade color, color image information, and an associated manufacturer.

In accord with the invention, each of the tabs 40 are illuminated by one or the handpieces 32a or 32b so that a color image is captured and stored in the medium 36. The image is accompanied by associated information about that shade, such as the manufacturer type, e.g., the Vita shade guide, and the particular shade, e.g., "A2." For example, FIG. 4 illustrates one storage block 42 of data for storage as digital memory and which is representative of one tooth shade. In particular, block 42a includes digital color image information, block 42b denotes the particular tooth shade, e.g. "A2," and block 42c denotes the manufacturer name, so that the associated tooth shade porcelain can be purchased from the correct manufacturer. Generally, the blocks 42b, 42c of data are represented by digital words that specify the information, while block 42a includes image data corresponding to both color and spatial information.

Preferably, the color image data within the block 42a is in a RGB format (i.e., Red, Green, Blue digital format, such as known to those skilled in the art) which specifies a color pixel within the image to an accuracy exceeding the number and color spread of the selected shade guides. For example, if sixteen shades are stored within the memory 36, then the bit-specificity required of the color-coded data within the image block 42a should span and discriminate at least those sixteen shades of white. For example, if each color of the RGB is specified at 3-bits each, then 256 standard colors are discernible by the system 29 to cover sixteen tooth shades. Greater color determination accuracy is achieved with increased color-coding. In addition, if all the manufacturers of tooth shades are loaded into the memory 36, then even more color-coded accuracy is required, e.g., 8-bit per RGB color.

The display of the color imagery within the digital data block 42a is known to those skilled in the art. Specifically, the RGB information within the data block 42a specifies the color for each pixel on the monitor 44, FIG. 2, which is similar in capability to the monitor 22 of FIG. 1. The particular video driver (not shown) used to drive the monitor 44 specifies and controls the color and image display as appropriate. The RGB format specifies a color corresponding to signals which produce a suitable color picture on the monitor having the reference colors defined by the RGB chromaticities.

Figure 5:
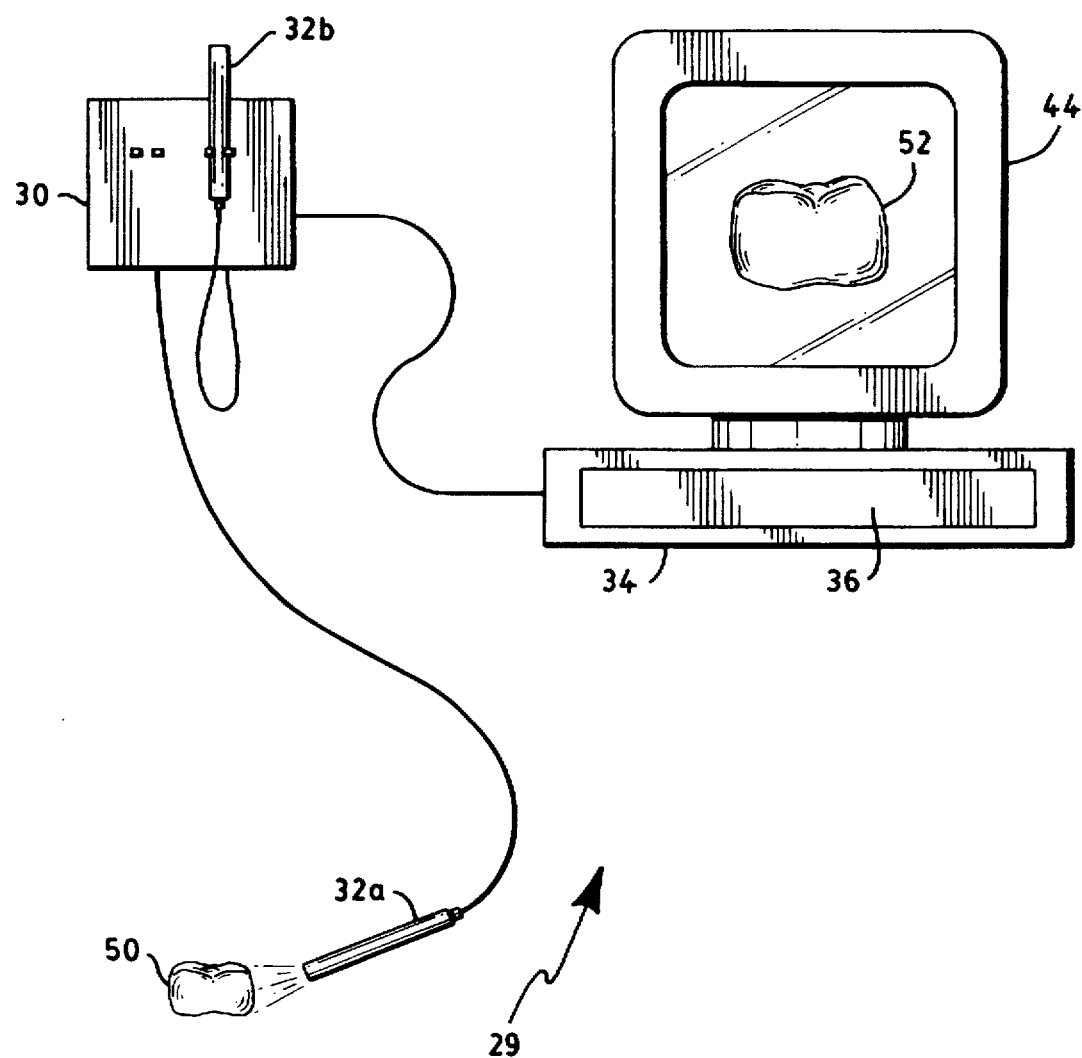
FIG. 5 shows an operational use of the system of FIG. 2.

Once the plurality of shades are loaded into memory 36, the system 29 is ready for use. FIG. 5 illustrates this process in more detail. A user illuminates the desired tooth 50, (illustratively shown outside of the patient's mouth) with the handpiece 32a such that an image 52 of the tooth 50 is displayed on the monitor 44. Although this step of forming an image on the screen 44 is not required, it helps to assess the accuracy to which the camera 30 captured the image 52.

As above, this image data 52 is stored into a block such as block 42, FIG. 4. The shade analyzer subsystem then compares the digital information within the block of data representing the image 52 with the blocks of data representative of the several tooth shades. In one embodiment, a comparison of the RGB values is made between the tooth image data 52 and the several shades to find a best fit or match.

It is important to note that this process has several advantages over the prior art. In particular, as long as the same camera 30 captures the data of the tooth shades and the patient's tooth shade data, it does not matter that the stored image color within the processor 34 match the perceived color or hue observed by a typical human. That is, as long as the data captured by the system 29 correlates to the same reference, e.g., the same camera 30, the match between the image 52 and the plurality of tooth shades will be calibrated automatically. This is in contrast to many of the prior art references, e.g., U.S. Pat. No. 5,383,020, which requires a sensitivity maxima of the human eye. The invention has no corresponding limitation because the camera of the system 29 objectively gathers the data from the same internal source. Nevertheless, it is preferable that the color display and coding of the camera 30 correspond to natural and perceived colors so that the image appears normal to a viewer.

Those skilled in the art should appreciate that the data from the plurality of tooth shades can also be loaded from a floppy disk into the subsystem 34. More particularly, the tooth shade data from the one or more manufacturers can be installed directly into the system 29 without physically capturing the image of each tooth shade, provided that the data is captured by a camera that is similar to the camera 30, or by a camera that is calibrated to within an acceptable margin to the camera 30. In this manner, a user of the system 29, e.g., a dentist, need never have actual tooth shade tabs at the office. Rather, the system 29 is used to capture color data on the patient's tooth; and the stored tooth shade information within the system 29 is automatically extracted, including a manufacturer identifier.

Figure 6:
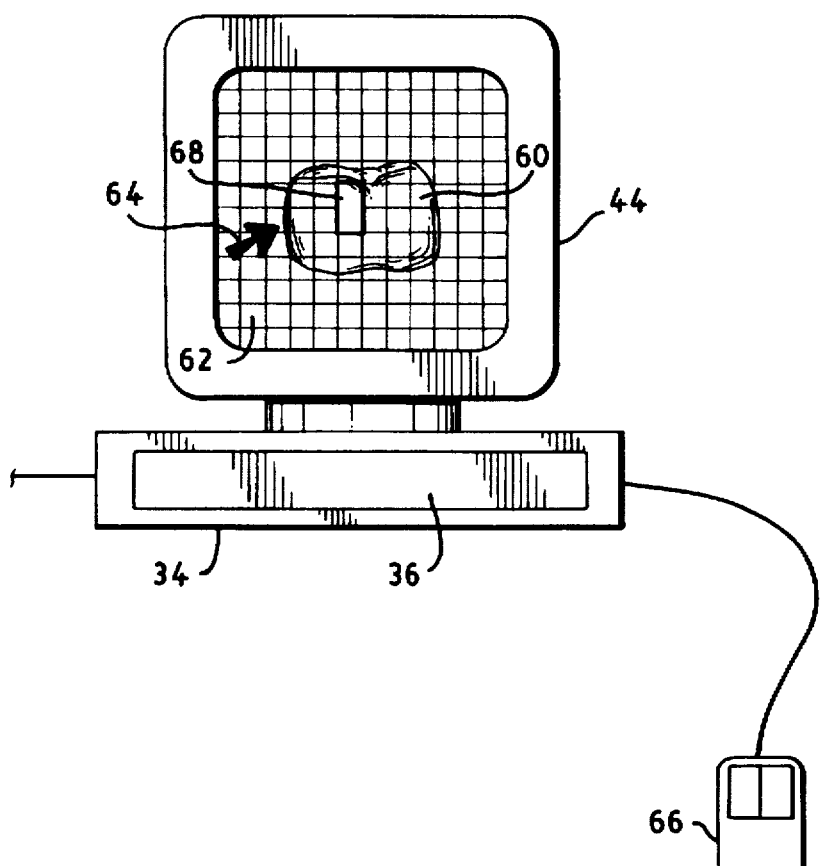
FIG. 6 illustrates image averaging and specification techniques, according to the invention.

It is worth noting that not all tooth shade information is readily derived from the patient. In particular, unlike the tooth shades from the shade guides, which are very uniform in color, a patient's tooth can include a myriad of different shades. Tooth stains and the like alter the tooth's color spatially, so that a selection or integration of color is preferred. FIG. 6 illustrates one embodiment of the invention for dealing with this non-uniformity.

Specifically, FIG. 6 shows a tooth image 60 of a patient's tooth on the monitor 44. Each pixel 62, which is grossly over-sized for illustrative purposes, corresponds to a different spatial location and color of the tooth's image 60. Accordingly, a user of the system 29 can select one of the pixels at the desired color by pointing and clicking a mouse pointer 64, via the mouse 66, at any selected location (the details of the mouse and mouse pointer are widely known to those skilled in the art without further reference hereto, and are shown for illustrative purposes only). This selected information is then stored with the block of data, e.g., block 42b of FIG. 4.

Alternatively, the image of the tooth 60 can be averaged over a selected area by selecting a particular region for which the color imagery is averaged. For example, if the tooth 60 is to be averaged over the two pixels identified by the outline 68, then the subsystem 29 averages the two RGB values and specifies the tooth shade match in block 42b as an average of the two.

Figure 7:
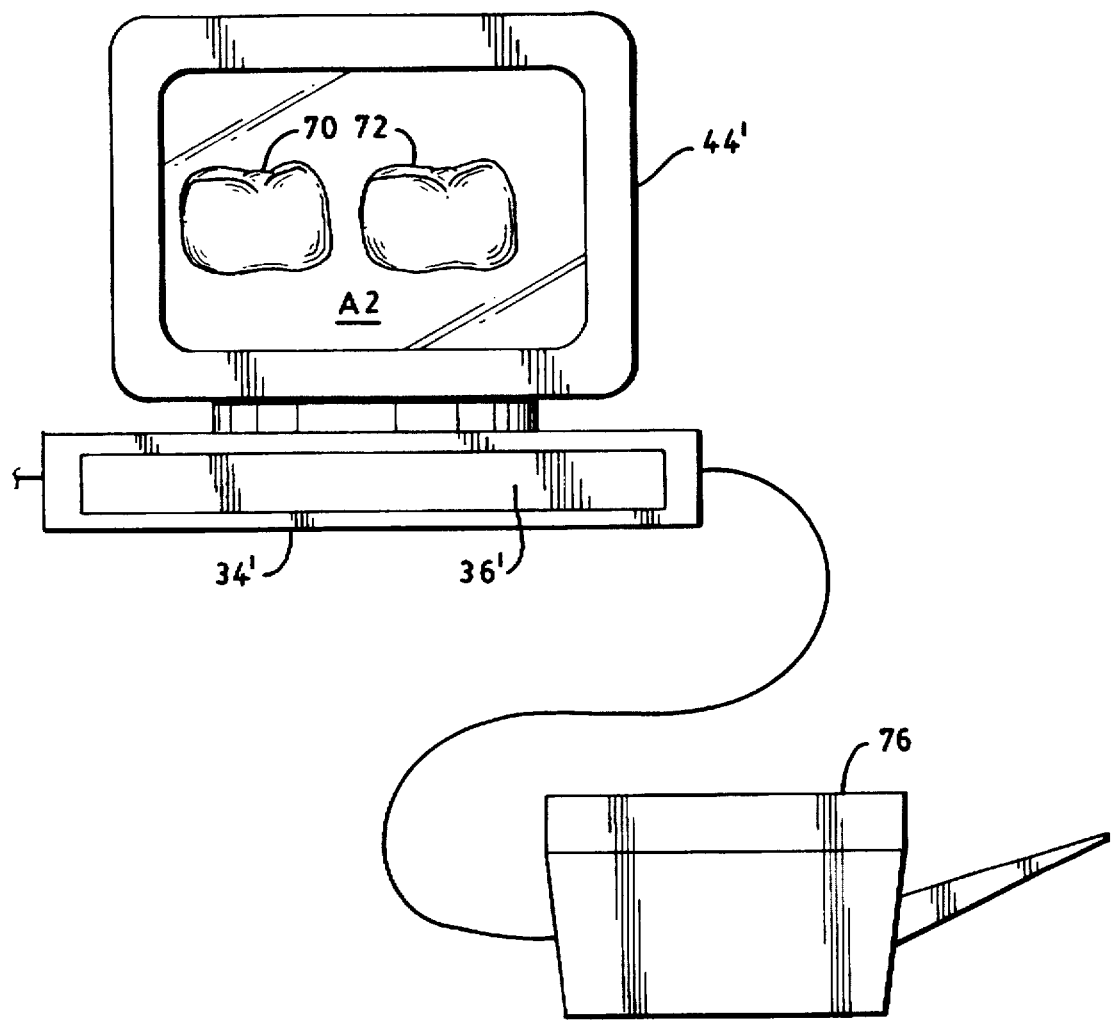
FIG. 7 illustrates an image comparison on the system of FIG. 2.

FIG. 7 illustrates another monitor 44' and subsystem 34' constructed according to the invention, each of which is similar to the monitor 44 and subsystem 34 of FIG. 2, respectively. In the illustrated embodiment, an image 70 of a patient's tooth is matched to the appropriate shade, as above, and then an image 72 of the matched shade is also displayed on the monitor 44'. The subsystem 34' further generates and displays the tooth shade identifying match, e.g., "A2," on the screen 44' so that the ordering information about the tooth reconstruction is easily ascertained. In the illustrated embodiment, a visual comparison between the tooth and the selected shade is made available to both the dentist and the patient. The display 44' can also display the particular porcelain product information.

It should be apparent to those skilled in the art that the data and information displayed on the monitor 44' can also be downloaded to a printer 76, so that a permanent record of the exam is obtained in hard-copy form.

In the event that the system 29 of FIG. 2 does not find a close match to one existing tooth shade, the subsystem 34 specifies a combination of tooth shades that correspond to the color of the patient's tooth image data, e.g., the image 52 of FIG. 5. Preferably, this information is determined in fractions of the appropriate shade, e.g., ½ "A2" and ½ "C4."Such fractions are determinable, according to one embodiment of the invention, by comparing the RGB data within the plurality of tooth shade blocks 42b with the actual patient's tooth shade image information. If the RGB data of the patient's tooth is equal to the chromaticity sum of ½ "A2" and ½ "C4," then such a fraction is entered into the match data block 42b for the selected tooth shade, and displayed on the screen 44 for the user. The chromaticity mathematics used to combine and subtract colors is known to those skilled in the art. Further detail may be found with reference to "Television Engineering Handbook," edited by K. Blair Benson, McGraw-Hill (1986), which is incorporated herein by reference.

The patient's tooth shade information is typically communicated to a laboratory which manufactures the reconstructed tooth via a plurality of porcelain coatings. This process of constructing porcelain layers onto a tooth model is known in the art; although the specification of the differing porcelain layers by data generated by an intraoral camera is specific to the invention. In the event that certain fractions of different porcelain layers are needed, such as described above, the system of the invention again provides and generates the appropriate shade fractions corresponding to the multiple layers.

Other color theory details, including the adding and subtracting of multiple colors, may be found with reference to the following patents, each of which is expressly incorporated herein by reference: U.S. Pat. No. 5,383,020, entitled "Method and apparatus for determining the color of a translucent object such as a tooth;" WO 86/03292, entitled "A spectrum-photometer device for exactly determining the colour of a dental plate and or dental pluggings;" U.S. Pat. No. 3,986,777 entitled "Tristimulus colorimeter for use in the fabrication of artificial teeth;" U.S. Pat. No. 4,654,794 entitled "Methods for determining the proper coloring for a tooth replica;" U.S. Pat. No. 4,836,674 entitled "Method and apparatus for determining color, in particular of a dental prosthesis;" U.S. Pat. No. 5,231,472 entitled "Color matching and characterization of surface coatings;" and U.S. Pat. No. 4,247,202 entitled "Automatic computing color meter."

Figure 8:
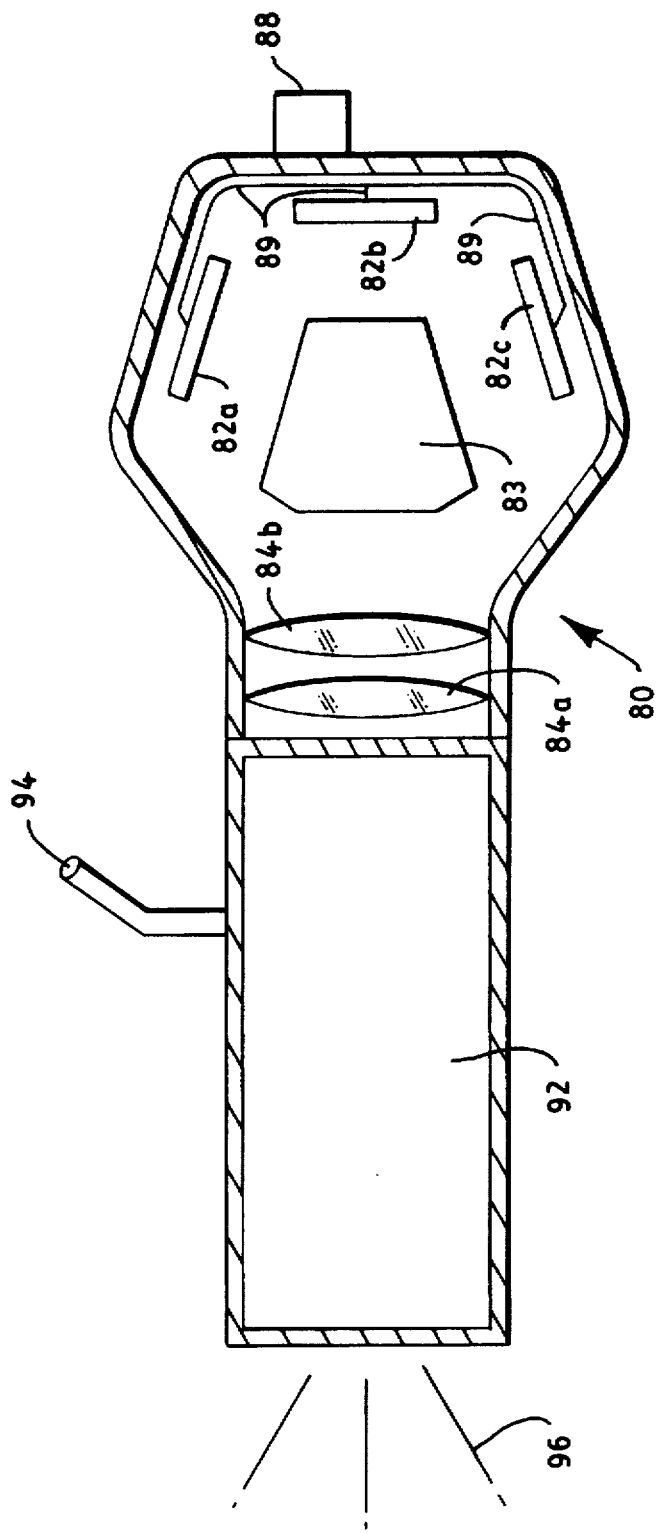
FIG. 8 illustrates a common aperature color CCD camera and handpiece constructed according to the invention, and which form another embodiment of a shade analyzer system.

FIG. 8 illustrates another embodiment of the invention, and which includes a common aperature color CCD camera 80. The camera 80 is commonly known as a "three-chip" color camera because of the three separate area CCD arrays (and preamplifiers) 82a, 82b, 82c. A complex prism 83 splits the light energy entering through the aperture lenses 84a, 84b into the three RGB color components. That is, each of the arrays 82 uniquely corresponds to one of the three color spectrums, such as Red. A housing 86 surrounds and protects the camera 80 from contact with external influences. The outputs from the three arrays 82a, 82b, 82c connect to a common RS232 interface 88, which is in turn connected, via signal lines 89, to a digital video processor shade analyzer subsystem, such as described above.

The size of the camera 80 is small, typically about 40 mm3 or less. One manufacturer of a camera 80 includes Richter Enterprises, of Del Norte, Colo., which makes the Model AD01 Common Aperture Camera.

The front aperture section 90 of the camera 80 connects to a handpiece 92—similar to the handpieces 32a, 32b described above—which is utilized by the dentist to illuminate and capture light imagery within the patient's mouth. For example, one acceptable handpiece 92 is an endoscopic handpiece which derives illumination from an external source 94, e.g., a lamp. The source is imaged through the endoscope to provide illumination 96 at the target area designated by the dentist; and the endoscope recaptures the light scattered from within the patient's mouth to form an image, in conjunction with the camera 80, at the several CCD arrays 82a, 82b, 82c.

Each of the CCDs 82a, 82b, 82c is coaligned with the other so that three distinct pixels, i.e., one each corresponding to R, G or B chromaticities, substantially view the same target point. Typically, each of the pixels specifies an 8-bit (or even 10-bit) color, so that, in total, the combination of the three arrays form a possible 256×256×256 colors. This provides sufficient resolution to discern several shades of white within the shade guides, so that a particular guide may be matched with a patient's tooth.

Figure 9:
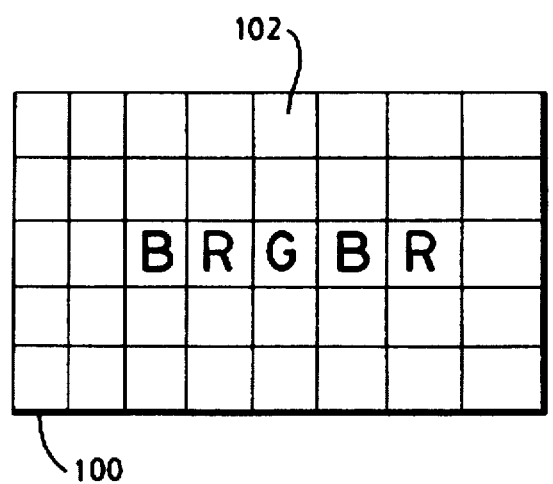
FIG. 9 shows an alternative CCD array technology, according to the invention, and which is suitable for use within the camera of FIG. 8.

Alternatively, the arrays of FIG. 8 can be replaced with a single array 100, FIG. 9 (as such, the prism 83 is also no longer required). Such an array 100 is popular in lower cost Camcorder technologies. In one embodiment, the array 100 has serial RGB pixels along each row of the array, here denoted as "R," "G" and "B" within each pixel 102. This scheme reduces resolution; although it also reduces costs. As above, each of the three RGB pixels is utilized to assess and determine shade color.

It should be apparent to those skilled in the art that certain modifications can be made to the invention as described herein without departing from the scope of the invention.

In view of the foregoing, what is claimed as new and secured by the letters patent is:

1. A method for comparing the tooth shade of a patient's tooth after the patient's teeth are cosmetically whitened, comprising the steps of:

capturing a first image of the patient's tooth with an intraoral camera before the tooth is cosmetically whitened, the first image including first color information representative of a color of the tooth, processing the color information of the image to determine the color of the patient's tooth, comparing the color of the patient's tooth to a plurality of tooth shades, the tooth shades being stored in an electronic medium, identifying one or more tooth shades with a combined color corresponding to the color of the patient's tooth, whitening the teeth, communicating the one or more identified tooth shades to a user of the system, and viewing the patient's tooth on a monitor after the whitening step while simultaneously displaying an image of the patient's pre-whitened tooth, to provide before and after imagery.

2. A system for determining the tooth shade of a patient's tooth, comprising:

a color CCD camera for capturing the image of the patient's tooth, the image including color information representative of a color of the tooth, the CCD camera comprising three CCD arrays, each of the arrays collecting image data corresponding to a color spectrum selected from the group of red, green and blue, and a shade analyzer sub-system connected for electrical communication with the CCD camera, the shade analyzer having (i) color processing means for determining the color of the patient's tooth from the color information of the image, (ii) storage means for storing shade information representative of a plurality of tooth shades, each of the tooth shades corresponding to a different tooth color, (iii) color correlation means for comparing the color of the patient's tooth to the plurality of tooth shades and for identifying a tooth shade with a color corresponding to the color of the patient's tooth, and (iv) means for communicating the identified tooth shade to a user of the system.

3. A system for determining the tooth shade of a patient's tooth comprising:

a color CCD camera for capturing the image of the patient's tooth, the image including color information representative of a color of the tooth, the CCD camera comprising a single CCD array, the array including a plurality of proximately located pixels corresponding to a color chromaticity selected from the group of red, green and blue, each of any group of three pixels having a different color associated therewith, and a shade analyzer sub-system connected for electrical communication with the CCD camera, the shade analyzer having (i) color processing means for determining the color of the patient's tooth from the color information of the image, (ii) storage means for storing shade information representative of a plurality of tooth shades, each of the tooth shades corresponding to a different tooth color, (iii) color correlation means for comparing the color of the patient's tooth to the plurality of tooth shades and for identifying a tooth shade with a color corresponding to the color of the patient's tooth, and (iv) means for communicating the identified tooth shade to a user of the system.

4. A system according to claim 3, further comprising means for integrating at least a portion of the tooth to determine an average color over the portion.

* * * * *

(12) EX PARTE REEXAMINATION CERTIFICATE (5065th)
United States Patent
Murljacic

(10) Number: US 5,766,006 C1
(45) Certificate Issued: Feb. 22, 2005

(54) TOOTH SHADE ANALYZER SYSTEM AND METHODS

(75) Inventor: Maryann Lehmann Murljacic, Darien, CT (US)

(73) Assignee: Tooth Shade Analyzing Technologies, Inc., Darien, CT (US)

Reexamination Request:
No. 90/006,247, Mar. 14, 2002

Reexamination Certificate for:
Patent No.: 5,766,006
Issued: Jun. 16, 1998
Appl. No.: 08/494,979
Filed: Jun. 26, 1995

(51) Int. Cl.[7] ............................................. A61C 19/10
(52) U.S. Cl. ........................................ 433/26; 356/408
(58) Field of Search ........................ 433/26, 29, 203.1, 433/215; 364/413.28; 356/402, 405, 406, 408

(56) References Cited

U.S. PATENT DOCUMENTS

| | | | |
|---|---|---|---|
| 3,405,446 A | 10/1968 | Wiener | 433/215 |
| 3,861,044 A | 1/1975 | Swinson, Jr. | 433/218 |
| 3,975,760 A | 8/1976 | Yamanaka et al. | 348/262 |
| 3,986,777 A | 10/1976 | Roll | 356/176 |
| 4,016,598 A | 4/1977 | Yamanaka | 348/265 |
| 4,106,056 A | 8/1978 | Nagumo et al. | 348/265 |
| 4,110,826 A | 8/1978 | Möllgaard et al. | 364/526 |
| 4,247,202 A | 1/1981 | Failes | 356/310 |
| 4,414,635 A | 11/1983 | Gast et al. | 364/526 |
| 4,518,258 A | 5/1985 | Broersma | 356/405 |
| 4,547,074 A | 10/1985 | Hinoda et al. | 356/405 |
| 4,575,805 A | 3/1986 | Moermann et al. | 364/474 |
| 4,591,900 A | 5/1986 | Heeb et al. | 348/277 |
| 4,616,933 A | 10/1986 | Lévêque et al. | 356/416 |
| 4,623,973 A | 11/1986 | Hoffrichter et al. | 364/526 |
| 4,654,794 A | 3/1987 | O'Brien | 364/413 |
| 4,657,399 A | 4/1987 | Hall | 356/421 |
| 4,692,481 A | 9/1987 | Kelly | 523/210 |
| 4,802,850 A | 2/1989 | Boon | 433/26 |
| 4,813,000 A | 3/1989 | Wyman et al. | 364/526 |
| 4,836,674 A | 6/1989 | Lequime et al. | 356/319 |
| 4,881,811 A | 11/1989 | O'Brien | 356/323 |
| 4,903,122 A | 2/1990 | Ozaki et al. | 348/237 |
| 4,919,617 A | 4/1990 | Antons et al. | 433/26 |
| 4,978,296 A | 12/1990 | Antons et al. | 433/26 |
| 5,012,431 A | 4/1991 | Stanziola | 364/526 |
| 5,055,040 A | 10/1991 | Clar | 433/26 |
| 5,124,797 A | 6/1992 | Williams et al. | 433/29 |
| 5,149,267 A | 9/1992 | Longhini et al. | 433/26 |
| 5,177,694 A | 1/1993 | Graham et al. | 364/526 |
| 5,231,472 A | 7/1993 | Marcus et al. | 356/402 |
| 5,240,414 A | 8/1993 | Thompson | 433/26 |
| 5,261,815 A | 11/1993 | Pozzi | 433/26 |
| 5,273,429 A | 12/1993 | Rekow et al. | 433/215 |
| 5,282,025 A | 1/1994 | Sato | 358/44 |
| 5,313,267 A | 5/1994 | MacFarlane et al. | 356/405 |
| 5,340,309 A | 8/1994 | Robertson | 433/69 |

(List continued on next page.)

FOREIGN PATENT DOCUMENTS

| | | | |
|---|---|---|---|
| DE | 26 41 740 A1 | 3/1978 | |
| EP | 0 360 657 | 3/1990 | |
| JP | 4-301530 | 10/1992 | 356/402 |
| JP | 4-338465 | 11/1992 | 433/203.1 |
| WO | WO 86/03292 | 6/1986 | |
| WO | WO 91/02955 | 3/1991 | 433/203.1 |
| WO | WO 95/15731 | 6/1995 | |

*Primary Examiner*—John J. Wilson

(57) ABSTRACT

An intraoral camera connects to a shade analyzer subsystem, e.g., a digital video processor, and a color display monitor. The camera captures a digital color image of the patient's tooth and the subsystem compares that image to a stored plurality of tooth shades. Each tooth shade is represented in a block of data, including color image data, a tooth shade digital word, and a manufacturer type. The patient's tooth image includes an RGB chromaticity representation that is scanned and compared with the several tooth shades stored in memory, and a match is determined and communicated to a user of the system. The methodology includes the specification of fractional tooth shades, if needed, corresponding to a plurality of porcelain films for manufacturing a reconstructed tooth.

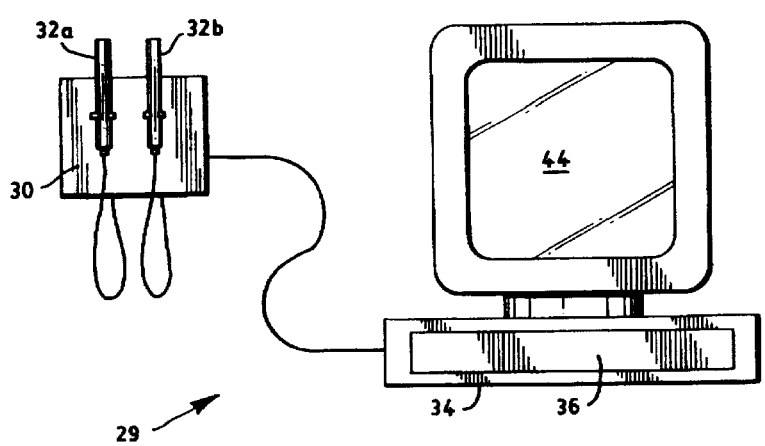

U.S. PATENT DOCUMENTS

| | | | |
|---|---|---|---|
| 5,373,364 A | 12/1994 | Krzyminski | 356/405 |
| 5,383,020 A | 1/1995 | Vieillefosse | 356/405 |
| 5,430,811 A | 7/1995 | Fukushima et al. | 382/254 |
| 5,431,562 A | 7/1995 | Andreiko et al. | 433/24 |
| 5,452,219 A | 9/1995 | Dehoff et al. | 364/474.05 |
| 5,453,009 A | 9/1995 | Feldman | 433/215 |
| 5,498,157 A | 3/1996 | Hall | 433/26 |
| 5,529,492 A | 6/1996 | Yarovesky et al. | 433/26 |
| 5,549,476 A | 8/1996 | Stern | 433/223 |
| 5,587,912 A | 12/1996 | Andersson et al. | 364/468.04 |
| 5,685,712 A | 11/1997 | Fischer | 433/26 |
| 5,692,900 A | 12/1997 | Fischer | 433/26 |
| 5,733,126 A | 3/1998 | Andersson et al. | 433/223 |

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claims 2 and 3 are determined to be patentable as amended.

Claim 4, dependent on an amended claim, is determined to be patentable.

New claims 5–17 are added and determined to be patentable.

2. A system for determining the tooth shade of a patient's tooth, comprising:
   a color CCD camera for capturing the image of the patient's tooth,
   the image including color information representative of a color of the tooth,
   the CCD camera comprising three CCD arrays, each of the arrays collecting image data corresponding to a color spectrum selected from the group of red, green and blue,
   and a shade analyzer sub-system connected for electrical communication with the CCD camera, the shade analyzer having
     (i) color processing means for determining the color of the patient's tooth from the color information of the image,
     (ii) storage means for storing shade information representative of a plurality of tooth shades, each of the tooth shades corresponding to a different tooth color,
     (iii) color correlation means for comparing the color of the patient's tooth to the plurality of *stored* tooth shades and for identifying a tooth shade with a color corresponding to the color of the patient's tooth, and
     (iv) means for communicating the identified tooth shade to a user of the system;
   *wherein the stored shade information comprises images taken by the same color CCD camera that is used to image the patient's tooth or by a similar color CCD camera that is calibrated to within an acceptable margin to the one used to image the patient's tooth.*

3. A system for determining the tooth shade of a patient's tooth comprising:
   a color CCD camera for capturing the image of the patient's tooth,
   the image including color information representative of a color of the tooth,
   the CCD camera comprising a single CCD array, the array including a plurality of proximately located pixels corresponding to a color chromaticity selected from the group of red, green and blue, each of any group of three pixels having a different color associated therewith,
   and a shade analyzer sub-system connected for electrical communication with the CCD camera, the shade analyzer having
     (i) color processing means for determining the color of the patient's tooth from the color information of the image,
     (ii) storage means for storing shade information representative of a plurality of tooth shades, each of the tooth shades corresponding to a different tooth color,
     (iii) color correlation means for comparing the color of the patient's tooth to the plurality of *stored* tooth shades and for identifying a tooth shade with a color corresponding to the color of the patient's tooth, and
     and (iv) means for communicating the identified tooth shade to a user of the system;
   *wherein the stored shade information comprises images taken by the same color CCD camera that is used to image the patient's tooth or by a similar color CCD camera that is calibrated to within an acceptable margin to the one used to image the patient's tooth.*

*5. A system according to claim 2 wherein the stored shade information comprises images of conventional shade guides taken by the same color CCD camera that is used to image the patient's tooth.*

*6. A system according to claim 2 wherein the stored shade information comprises images of conventional shade guides taken by a similar color CCD camera that is calibrated to within an acceptable margin to the one used to image the patient's tooth.*

*7. A system according to claim 2 which includes a color monitor display of color images of the tooth and stored tooth shades, with the shade analyzer sub-system communicating a tooth color representative of the identified tooth shade to the monitor, thereby providing a user of the system with a visual comparison of the patient's tooth color and the color of the identified tooth shade.*

*8. A system accordingly to claim 2 which further comprises:*
   *a light source, and*
   *an endoscopic handpiece operatively associated with the light source to provide illumination of the patient's tooth and to capture light imagery from the tooth to form in conjunction with the camera an image of the tooth, wherein the front aperture section of the camera is connected to the handpiece.*

*9. A system according to claim 8 wherein the handpiece derives illumination from an external light source.*

*10. A system according to claim 2 wherein the storage means is a computer hard disk or floppy disk storage medium that includes digital color images of the plurality of tooth shades.*

*11. A system according to claim 3 wherein the stored shade information comprises images of conventional shade guides taken by the same color CCD camera that is used to image the patient's tooth.*

*12. A system according to claim 3 wherein the stored shade information comprises images of conventional shade guides taken by a similar color CCD camera that is calibrated to within an acceptable margin to the one used to image the patient's tooth.*

*13. A system according to claim 3 which includes a color monitor display of color images of the tooth and stored tooth shades, with the shade analyzer sub-system communicating a tooth color representative of the identified tooth shade to the monitor, thereby providing a user of the system with a* visual comparison of the patient's tooth color and the color of the identified tooth shade.

14. A system accordingly to claim 3 which further comprises:
   a light source, and
   an endoscopic handpiece operatively associated with the light source to provide illumination of the patient's tooth and to capture light imagery from the tooth to form in conjunction with the camera an image of the tooth, wherein the front aperture section of the camera is connected to the handpiece.

15. A system according to claim 14 wherein the handpiece derives illumination from an external light source.

16. A system according to claim 3 wherein the storage means is a computer hard disk or floppy disk storage medium that includes digital color images of the plurality of tooth shades.

17. A system for determining the tooth shade of a patient's tooth comprising:
   a color CCD camera for capturing the image of the patient's tooth,
   the image including color information representative of a color of the tooth,
   the CCD camera comprising one of a single CCD array, the array including a plurality of proximately located pixels corresponding to a color chromaticity selected from the group of red, green and blue, each of any group of three pixels having a different color associated therewith, or three CCD arrays, each of the arrays collecting image data corresponding to a color spectrum selected from the group of red, green and blue,
   a shade analyzer sub-system connected for electrical communication with the CCD camera, the shade analyzer having
   (i) color processing means for determining the color of the patient's tooth from the color information of the image,
   (ii) storage means storing shade information representative of a plurality of tooth shades, each of the tooth shades corresponding to a different tooth color,
   (iii) color correlation means for comparing the color of the patient's tooth to the plurality of stored tooth shades and for identifying a tooth shade with a color corresponding to the color of the patient's tooth, and
   (iv) means for communicating the identified tooth shade to a user of the system; and
   means for integrating at least a portion of the tooth to determine an average color over the portion.

* * * * *